US010526308B2

(12) United States Patent
Taarning et al.

(10) Patent No.: US 10,526,308 B2
(45) Date of Patent: Jan. 7, 2020

(54) ADIPATE-TYPE COMPOUNDS AND A PROCESS OF PREPARING IT

(71) Applicant: HALDOR TOPSØE A/S, Kgs. Lyngby (DK)

(72) Inventors: Esben Taarning, Frederiksberg (DK); Amanda Birgitte Sølvhøj, Værløse (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 16/096,103

(22) PCT Filed: May 4, 2017

(86) PCT No.: PCT/EP2017/060702
§ 371 (c)(1),
(2) Date: Oct. 24, 2018

(87) PCT Pub. No.: WO2017/191282
PCT Pub. Date: Nov. 9, 2017

(65) Prior Publication Data
US 2019/0144415 A1 May 16, 2019

(30) Foreign Application Priority Data
May 4, 2016 (DK) .................................. 2016 00273

(51) Int. Cl.
*C07C 57/02* (2006.01)
*C07C 69/593* (2006.01)
*C07D 321/00* (2006.01)
*C07C 67/475* (2006.01)
*C07C 69/732* (2006.01)

(52) U.S. Cl.
CPC .......... *C07D 321/00* (2013.01); *C07C 67/475* (2013.01); *C07C 69/732* (2013.01); *C07B 2200/09* (2013.01)

(58) Field of Classification Search
CPC .............................. C07C 69/593; C07C 57/02
USPC ........................................... 560/181; 562/595
See application file for complete search history.

(56) References Cited

U.S. PATENT DOCUMENTS 4,400,468 A 8/1983 Faber
2009/0264672 A1 10/2009 Abraham et al.

FOREIGN PATENT DOCUMENTS

| EP | 2184270 A1 | 5/2010 |
| WO | 97/20865 A1 | 6/1997 |
| WO | 2007/093013 A1 | 8/2007 |
| WO | 2014/043182 A2 | 3/2014 |
| WO | 2016/083137 A1 | 6/2016 |

OTHER PUBLICATIONS

Danish Search Report dated Dec. 22, 2016, issued by the Danish Patent and Trademark Office in the corresponding Danish Patent Application No. PA 2016 00273.
Dewaele, A. et al., "Immobilized Grubbs Catalysts on Mesoporous Silica Materials: Insight Into Support Characteristics and Their Impact on Catalytic Activity and Product Selectivity", Catalysis Science 8 Technology, vol. 6, pp. 2580-2597, 2016.
Dewaele, A., "Synthesis Of Novel Renewable Polyesters and Polyamides With Olefin Metathesis", ACS Sustainable Chem. Eng. vol. 4, pp. 5943-5952, 2016.
Dusselier, M. et al., "Shape-Selective Zeolite Catalysis for Bioplastics Production", Green Chemistry, vol. 349, Issue 6243, pp. 78-80, 2015.
Dusselier, M. et al., "Toward Functional Polyester Building Blocks From Renewable Glycolaldehyde With Sn Cascade Catalysis", American Chemical Society Catalysis, vol. 3, pp. 1786-1800, 2013.
Farmer, T. J. et al., "Synthesis of Unsaturated Polyester Resins From Various Bio-Derived Platform Molecules", Int. J. Mol. Sci., vol. 16, pp. 14912-14932, 2015.
Freiria, M. et at., "A Practical Route for the Preparation of Substituted 6-oxo-2-Hexenoate Derivatives", SYNLETT, No. 6, pp. 805-808, 2003.
International Search Report (PCT/ISA/210) dated Sep. 5, 2017, by the European Patent Office as the International Searching Authority for International Application No. PCT/EP2017/060702.
Lund, A. K. et al., "The Effects of α-Pinene Versus Toluene-Derived Secondary Organic Aerosol Exposure on the Expression of Markers Associated With Vascular Disease", Inhalation Toxicology, vol. 25, No. 6, pp. 309-324, 2013.
Niemela, K. et al., "Non-Oxidative and Oxidative Alkaline Degradation of Pectic Acid", Carbohydrate Research, vol. 144, pp. 87-92, 1985.
Orazov, M. et al., "Tandem Catalysis for the Production of Alkyl Lactates From Ketohexoses at Moderate Temperatures", PNAS, vol. 112, No. 38, pp. 11777-11782, Sep. 22, 2015.
Solvhoj, A. et al., "Methyl Vinyl Glycolate as a Diverse Platform Molecule", Green Chemistry, vol. 18, pp. 5448-5455, 2016.
Written Opinion (PCT/ISA/237) dated Sep. 5, 2017, by the European Patent Office as the International Searching Authority for International Application No. PCT/EP2017/060702.
Invitation to Pay Additional Fees and, Where Applicable, Protest Fee and Annex to Form (PCT/ISA/206), Communication Relating to the Results of the Partial International Search, dated Jul. 14, 2017, by the European Patent Office as the International Searching Authority for International Application No. PCT/EP2017/060702.
Kuhn, R. et al. "Ring Closures With Esters of .Alpha., Delta.-Dihydroxymuconic Acid", 4 pages, XP-002771435, 1951.

*Primary Examiner* — Charanjit Aulakh
(74) *Attorney, Agent, or Firm* — Buchanan Ingersoll & Rooney P.C.

(57) ABSTRACT

The present invention regards new adipate-type compounds suitable as an intermediate in organic chemistry, a platform chemical for the production of other chemicals, and as a monomer and co-monomer useful for the preparation of polymers and copolymers. The invention also regards the process of preparing the new adipate-type compounds from bio-based raw materials such as sugars.

24 Claims, No Drawings

ADIPATE-TYPE COMPOUNDS AND A PROCESS OF PREPARING IT

TECHNICAL FIELD

The present invention regards a new compound suitable as an intermediate in organic chemistry, a platform chemical for the production of other chemicals, and as a monomer and co-monomer useful for the preparation of polymers and co-polymers. The invention also regards the process of preparing the new compound from bio-based raw materials such as sugars.

BACKGROUND

In the chemical industry there is a great need for low-cost functionalized molecules that can be used for the production of polymers with improved performance characteristics. Polyesters comprise monomers with at least two chemical groups capable of binding together and forming a polymer chain. Molecules containing more than two functional groups can be desirable to use in polyester synthesis since they often lead to modified performance characteristics. Often such molecules are made via a complex chemical synthesis and require multiple processing steps, making them expensive and difficult to obtain. It is therefore relevant to find simple, low-cost ways of producing such molecules. In recent years, much attention has been directed towards developing efficient methods for obtaining chemical building blocks from renewable bio-based sources. Such molecules which can be produced directly from biomass at low cost, and which have the potential to be used for the synthesis of other chemicals, may be referred to as 'platform molecules'.

One platform molecule which is available from renewable sources, is methyl vinyl glycolate (methyl 2-hydroxybut-3-enoate, MVG). It is available e.g. by zeolite catalyzed degradation of mono- and/or disaccharides, such as described in EP 2 184 270. MVG has the potential to become an important renewable platform molecule for commercially relevant applications. MVG is a small molecule with a simple structure, and yet it possesses several functional groups, providing it with ample handles for many different chemical transformations.

Recently the formation of a vinyl glycolide dimer from 2-hydroxybut-3-enoic acid has been achieved in up to 24% yield, employing a shape selective zeolite catalyst (M. Dusselier, P. Van Wouwe, A. Dewaele, P. A. Jacobs, B. F. Sels, Science 2015, 349, 78-80).

MVG has also been copolymerized with lactic acid (LA), thus providing the possibility of tuning the properties of poly-lactic acid (PLA)-based polymers. This can be done either by varying the ratio between MVG and LA or through functionalization of the reactive vinyl side chain of the MVG units (M. Dusselier, P. Van Wouwe, S. De Smet, R. De Clercq, L. Verbelen, P. Van Puyvelde, F. E. Du Prez, B. F. Sels, ACS Catal. 2013, 3, 1786-1800).

Grubbs catalysts immobilized on silica supports have been tested on various substrates for catalytic activity and product selectivity. In Table 6, entry 8, butyl vinyl glycolate was converted in nonane as solvent in the presence of $2^{nd}$ generation Hoveyda-Grubbs catalyst into an adipate-type compound. However, the yield is very low, and the end product does not crystallize.

There is still a need for highly functionalized platform molecules which can be produced from renewable sources and by simple methods.

SUMMARY OF INVENTION

According to the present invention a novel adipate-type compound is provided, of the formula I:

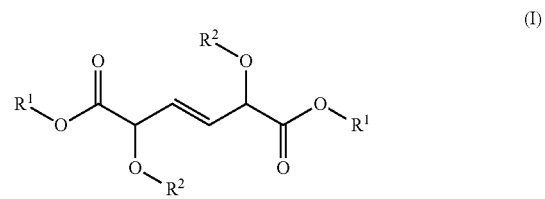

wherein $R^1$ is selected from the group consisting of H—; and $C_1$-$C_2$ alkyl; and $R^2$ is selected from the group consisting of —H; and —$CH_3$.

R1 may be substituted with a heteroatom selected from |N and O|.[ALT[1]]

Such adipate-type compounds are highly functionalized and possess advantageous characteristics as platform molecules (or base chemical/intermediate) for the chemical industry such as for producing polyesters. They may be polymerized or copolymerized with other monomers, such as e.g. lactic acid.

The adipate-type compound of the formula (I) is a structurally interesting molecule for which many applications can be envisioned. The 1,6-diester structure resembles the structure of adipic acid, and therefore the compound of formula I can be utilized in similar applications, such as building blocks for polymers. Unlike adipic acid though, the adipate type dimer of the formula (I) possesses two substituents ($R^2$) which introduces the possibility of using it as a functionalized polyester monomer. Polymerization of polymers derived from the building blocks of the present invention have been described in the article "Synthesis of Novel Renewable Polyesters and Polyamides with Olefin Metathesis", Dewaele, Annelies, Meerten, Lotte, Verbelen, Leander, Eyley, Samuel, Thielemans, Wim, Van Puyvelde, Peter, Dusselier, Michiel, Sels, Bert, ACS Sustainable Chem. Eng. 2016, 4 (11) pp 5943-5962.

In an aspect of the present invention $R^2$ is —H. In another aspect of the present invention R1 is selected from the group consisting of —H, —$CH_3$, and —$CH_2CH_3$. In a further aspect of the present invention $R^1$ and $R^2$ each are —$CH_3$. In yet a further aspect, $R^1$ is $C_1$-$C_2$ alkyl and $R^2$ is H. In another aspect of the present invention the C—C double bond of the compound of formula I is in (E)-configuration.

The adipate-type compounds of the formula (I) may according to the present invention be prepared by a process comprising the steps of:

i) providing a compound of the formula:

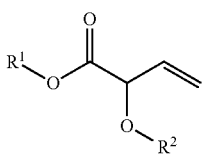

(II)

wherein
R1 is selected from the group consisting of H—; and $C_1$-$C_2$ alkyl and R2 is selected from the group consisting of —H; and —$CH_3$;
ii) providing a catalyst material catalyzing a metathesis reaction;
iii) converting the compound of i) in the presence of the catalytic material of ii); and
iv) recovering a reaction product comprising a compound of the formula (I).

R1 may be substituted with a heteroatom selected from |N and O|.

Generally, the process will be carried out by adding a feed comprising compound (II) and the catalyst material to a reaction vessel. Generally stirring is preferred.

A "catalyst material catalyzing a metathesis reaction" or a "metathesis catalyst material" for use in the process according to the present invention is any material catalyzing a metathesis reaction such as described in US 2009/0264672. A suitable metathesis catalyst is accordingly a material comprising a compound of the general formula (XI):

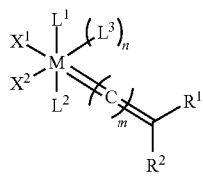

(XI)

Wherein
M is a transition metal, such as ruthenium, molybdenum, osmium, chromium, rhenium and tungsten, and preferably a group 8 transition metal;
$L^1$, $L^2$ and $L^3$ are each neutral electron donor ligands;
n is 0 or 1, so that L3 may or may not be present;
m is 0, 1 or 2;
$X^1$ and $X^2$ are each anionic ligands; and
$R^1$ and $R^2$ are each independently selected from the group consisting of hydrogen, hydrocarbyl, substituted hydrocarbyl, heteroatom containing hydro-carbyl, substituted heteroatom containing hydro-carbyl, and functional groups.

The catalyst material may be used in a homogeneous form or in a heterogeneous form, such as immobilized on a support, such as described in "Immobilized Grubbs Catalyst on Mesoporous silica materials: insight into support characteristics and their impact on catalytic activity and product selectivity", Dewaele, Annelies, Van Berlo, Boris, Dijkmans, Jan, Jacobs, Pierre A., Sels, Bert F, Catal. Sci. Technol., 2016, 6, 2580-2597.

In an embodiment, the compound (II) is provided in the form of a feed, which comprises at least 50 wt % of the compound (II). The substrate and the catalyst material of step ii) are mixed in step iii) to form a reaction mixture and the conversion in step iii) of compound (II) in to compound (I) takes place within the reaction mixture. Optionally also solvent is added. Preferably the mixture is exposed to mixing and preferably the mixing and converting takes place in a suitable reaction vessel, such as a stirred tank reactor. Ethylene formed during the conversion is preferably removed, since it can lower the activity of the catalytic material.

According to an aspect of the present invention, the compound of formula (I) is recovered as a composition comprising the compound of the formula (I). The composition may be the reaction product recovered in step iv) of the process according to the invention. Accordingly, the composition may further comprise a solvent and/or catalyst material. In an embodiment, the composition comprises at least 80 wt % such as at least 90, 95, 97 wt %, or such as 80-100, 90-100, 95-100 or 97-100 wt % of the (E)-isomer of the compound of formula (I).

The conversion of step iii) is preferably conducted with stirring and it is preferably conducted at a temperature in the range of from 20 to 120° C., more preferred of from 30 to 100° C. The period of time that the heating is applied in step iii) is preferably in the range of from 5 minutes to 24 hours. In and embodiment, the pressure is in the range of from 1 to 1000 kPa, such as from 10-125 kPa.

The compound (II) may be dissolved in an organic solvent, such as methyl lactate, ethyl lactate, toluene or dichloromethane, or mixtures thereof. The solvent is preferably miscible with the compound (II) and the catalyst material, but not with the compound produced (compound (I)). Preferably, the initial concentration of the compound (II) in the reaction mixture is at least 5 wt %, such as in the range of from 5-90 wt %, or 10-90 wt %.

In an embodiment, step iii) is conducted without the addition of solvent. Accordingly, the reaction mixture comprises at least 50 wt % of the compound (II) and the rest may be other products from the preparation of compound (II), e.g. alkyl lactates, such as methyl and/or, ethyl lactate. Preferably, the reaction mixture comprises from 50 to 99.9 wt % of the compound (II), such as from 70 to 99.9, 80 to 99.9 or 95 to 99.9 wt % An advantage of not using a solvent in step iii) of the process of producing the compound of formula I is that there is no solvent to remove after the conversion is completed. For the process according to the present invention, the yield of compound I has surprisingly shown to increase when no solvent was added. When no solvent is added in step iii) the conversion of compound (II) is also referred to as taking place in a solvent-free environment. When the conversion is carried out in a solvent-free environment, more than 95% of the reaction product is surprisingly recovered in (E)-configuration (or as the (E)-isomer). This is an advantage, since the (E)-configuration is more stable than the (Z)-configuration. Without being bound by theory, the inventors believe, that the solvent-free environment provides that the more abundant isomer will precipitate. At the same time the two isomers will be in equilibrium, and thus the more abundant isomer will continue to precipitate and the less abundant will convert into the more abundant one little by little. This equilibrium between the two isomers is catalyzed by the metathesis catalyst. If an organic solvent is present, however, this phenomenon is not observed, probably due to lack of precipitation of the (E)-isomer.

An advantage of converting the compound (II) in a solvent-free environment allows a low loading of catalyst material. In an embodiment, the catalyst loading is from 1 to 10,000 ppm of catalyst relative to compound (II) on a molar basis.

The recovery of reaction product in step iv) may be a simple collection of the reaction product resulting from the conversion. The reaction product may be exposed to a purification such as removal of any solvent or removal of any byproducts or reactants. Purification may be conducted by distillation, column chromatography or other suitable method.

The process may be conducted using a batch reactor or a continuous reactor (reaction vessel).

In general the reaction scheme for homo metathesis of vinyl glycolic acid and ester derivatives of vinyl glycolic acid (compound II where $R^2$=H) forming an adipate-type compound may be depicted as follows:

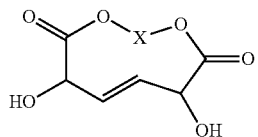

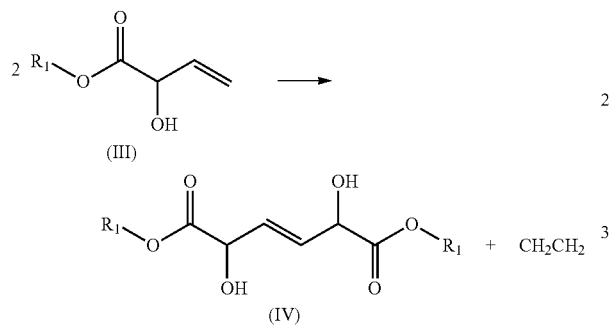

Wherein $R_1$=H in the case the substrate is vinyl glycolic acid also known as 2-hydroxy-3-butenoic acid (VGA) and the adipate-type compound is 2,5-dihydroxy-hex-3-enedioic acid; $R_1$=$CH_3$ in the case the substrate is methyl vinyl glycolate (MVG) also known as methyl 2-hydroxy-3-butenoate and the adipate-type compound is 2,5-dihydroxy-hex-3-enedioic acid dimethyl ester; $R_1$=$CH_2CH_3$ in the case the substrate is ethyl vinyl glycolate (EVG) also known as ethyl 2-hydroxy-3-butenoate and the adipate-type compound is 2,5-dihydroxy-hex-3-enedioic acid diethyl ester; $R_1$=$CH_2CH_2CH_3$ in the case the substrate is propyl 2-hydroxy-3-butenoate and the adipate-type compound is 2,5-dihydroxy-hex-3-enedioic acid dipropyl ester; $R_1$=$CH(CH_3)_2$ in the case the substrate is isopropyl 2-hydroxy-3-butenoate and the adipate-type compound is 2,5-dihydroxy-hex-3-enedioic acid diisopropyl ester; $R_1$=$CH_2CH_2CH_2CH_3$ in the case the substrate is butyl 2-hydroxy-3-butenoate and the adipate-type compound is 2,5-dihydroxy-hex-3-enedioic acid dibutyl ester or $R_1$=any $C_1$-$C_{12}$ alkyl group in which case the substrate is $C_1$-$C_{12}$ alkyl 2-hydroxy-3-butenoate and the adipate-type compound is 2,5-dihydroxy-hex-3-enedioic acid di($C_1$-$C_{12}$ alkyl) ester.

2,5-dihydroxy-hex-3-enedioic acid (compound (IV), when $R^1$=H) and 2,5-dihydroxy-hex-3-enedioic acid dimethyl ester (compound (IV), when $R^1$=$CH_3$) can be transformed one into the other by standard esterification or hydrolysis procedures, respectively.

According to an aspect of the present invention another novel adipate-type compound is provided of the formula V:

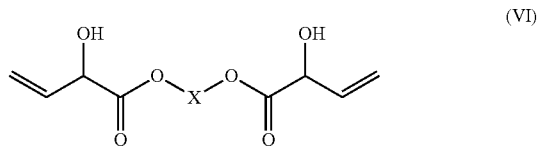

wherein
X=$(CH_2)_n$ [n=2-6]
or
X=$CH_2CH(CH_3)CH_2$
or
X=$CH_2C(CH_3)_2CH_2$
and preferably, n is 2 or 3.

The compounds of formula (V) are also highly functionalized and possess advantageous characteristics as platform molecules (or base chemical/intermediate) for the chemical industry such as for producing polyesters. They are also suitable as monomers for ring opening polymerization reactions.

The adipate-type compounds of formula (V), may according to the present invention be prepared by a process comprising the steps of:
i) providing a compound of the formula (VI):

wherein
X=$(CH_2)_n$ [n=2-6]
or
X=$CH_2CH(CH_3)CH_2$
or
X=$CH_2C(CH_3)_2CH_2$
and preferably, n is 2 or 3;
ii) providing a catalyst material catalyzing a metathesis reaction;
iii) converting the compound of i) in the presence of the catalyst material of ii); and
iv) recovering the reaction product comprising a compound of the formula (V).

Generally, the process will be carried out by adding a feed comprising compound (IV) and the catalyst material to a reaction vessel. Generally stirring is preferred.

The catalyst material may be used in a homogeneous form or in a heterogeneous form, such as immobilized on a support as described earlier.

In an embodiment, the compound (VI) is provided in the form of a feed, which comprises from 10 to 50 wt % of the compound (VI). The feed and the catalyst material of step ii) are mixed in step iii) to form a reaction mixture and the conversion in step iii) of compound (VI) into compound (V) takes place within the reaction mixture. Optionally the reaction mixture also contains a solvent. Preferably the mixture is exposed to mixing and preferably the mixing and converting takes place in a suitable reaction vessel, such as a stirred tank reactor. Ethylene formed during the conversion is preferably removed, since it can lower the activity of the catalytic material.

The process may be conducted using a batch reactor or a continuous reactor (reaction vessel).

According to an aspect of the present invention, the compound of formula (V) is recovered as a composition comprising the compound of the formula (V). The composition may be the reaction product recovered in step iv) of the process according to the invention. Accordingly, the composition may further comprise a solvent and/or catalyst material.

The conversion of step iii) is preferably conducted with stirring and it is preferably conducted at a temperature in the range of from 20 to 120° C., more preferred of from 30 to 100° C. The period of time that the heating is applied in step iii) is preferably in the range of from 5 minutes to 24 hours. In an embodiment, the pressure is in the range of from 1 to 1000 kPa, such as from 10-125 kPa.

The compound (VI) may be dissolved in an organic solvent, such as methyl lactate, ethyl lactate, toluene or dichlormethane, or mixtures thereof. The solvent is preferably miscible with the compound (VI) and the catalyst material, but not with the compound produced (compound (V)). Preferably, the initial concentration of the compound (VI) in the reaction mixture is at least 5 wt %, such as in the range of from 5-80 wt %, or 10-70 wt %.

The recovery of reaction product in step iv) may be a simple collection of the reaction product resulting from the conversion. The reaction product may be exposed to a purification such as removal of any solvent or removal of any byproducts or reactants. Purification may be conducted by distillation, column chromatography or other suitable method.

In a particular embodiment of the invention, the substrate is 2-hydroxy-but-3-enoic acid 2-(2-hydroxy-but-3-enoyloxy)-ethyl ester (compound VII)) which upon metathesis reaction is converted into the adipate-type compound 6,9-dihydroxy-2,3,6,9-tetrahydro-[1,4]dioxecine-5,10-dione (see compound (VIII) in the scheme below

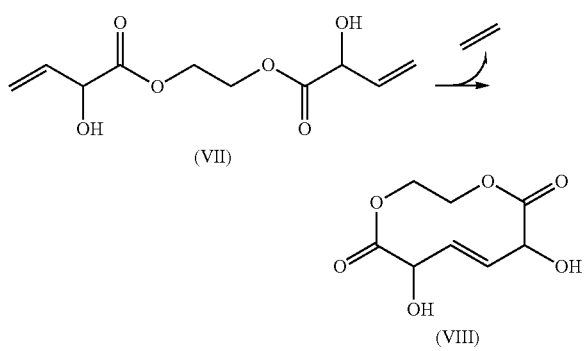

In yet another particular embodiment of the invention, the substrate is 2-hydroxy-but-3-enoic acid 3-(2-hydroxy-but-3-enoyloxy)-propyl ester (compound (IX)) which upon metathesis is converted into the adipate-type compound 7,10-dihydroxy-1,5-dioxa-cycloundec-8-ene-6,11-dione (see compound (X) in the scheme below).

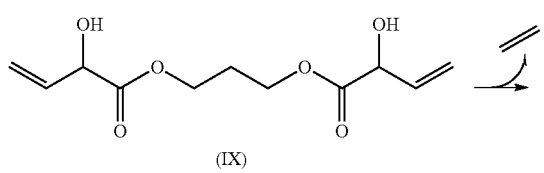

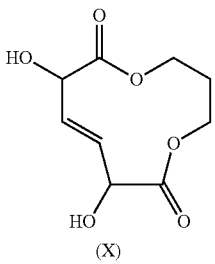

compounds of the formula (V) and specifically of the formula (VIII) and (X) are also suitable as monomers for ring opening polymerization reactions.

The compounds of formula (VI) may be prepared from MVG by conducting a transesterification reaction as described in example 2.

The adipate-type compounds according to the present invention are suitable as intermediates in the production of alternating co-polymers. In particular, they are suitable as co-monomers in the production of polyesters and polyamides. Their chemical structure enables them to be used as di-acids in combination with diols such as 1,2-ethanediol, 1,3-propanediol, 1,4-butanediol, 1,5-pentanediol and 1,6-hexanediol, cyclohexane dimethanol, or other similar linear diols for the synthesis of $[A-B]_n$ type co-polyesters. Similarly, the adipate-type compounds can be used as di-acids in combination with diamines such as 1,2-diaminoethane, 1,3-diaminopropane, 1,4-diaminobutane, 1,5-diaminopentane and 1,6-diaminohexane, para-phenylenediamine, or other similar diamines for the synthesis of $[A-B]_n$ type co-polyamides. The resulting polyester and polyamide materials obtained contain the secondary alcohol and olefin moieties from the adipate-type compounds in their backbone, allowing for further functionalization of the polymer if desired. Furthermore, the adipate-type compounds can be used as comonomers in poly(lactic acid) and poly(glycolic acid) polyester materials either by conversion first to cyclic [1,4] dioxane-2,5-dione compounds together with lactic acid, glycolic acid or vinyl glycolic acid followed by co-polymerization with lactide, or by direct reaction with lactic acid or glycolic acid.

When the vinyl glycolate substrate is reacted in the absence of solvent, the yield of adipate type compound has shown to be particularly high. Accordingly, yields as high as 70%, 75%, 80%, 85%, 90% or even as high as 91, 92, 93, 94 or 95% have been obtained.

Preferred catalysts according to the invention are Grubbs $2^{nd}$ generation catalysts and Hoveyda-Grubbs $2^{nd}$ generation catalyst. In particular, Grubb's $2^{nd}$ generation catalysts and Hoveyda-Grubbs $2^{nd}$ generation catalysts have been found to give a high yield of the adipate type compound and the amount of catalyst necessary was low. Accordingly, the $2^{nd}$ generation catalyst gave an isolated yield of 75% of 2,5-dihydroxy-hex-3-enedioic acid dimethyl ester with a 0.4% loading of catalyst.

Accordingly, a preferred catalytic material of step ii) comprises a catalyst of the formula:

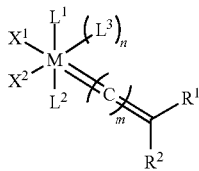

(XI)

wherein
M is a transition metal, for example ruthenium, molybdenum, osmium, chromium, rhenium and tungsten, and preferably a group 8 transition metal;
$L^2$ and $L^3$ are neutral electron donor ligands;
n is 0 or 1;
m is 0, 1 or 2;
$X^1$ and $X^2$ are anionic ligands;
$R^1$ and $R^2$ are each selected independently from the group consisting of hydrogen, hydrocarbyl, substituted hydrocarbyl, heteroatom containing hydro-carbyl, substituted heteroatom containing hydro-carbyl, and functional groups; and
$L^1$ is a carbene of the formula:

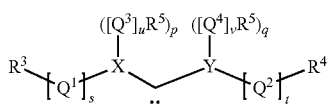

(XII)

wherein
Y and X are heteroatoms, such as N, O, S or P, and if X and/or Y are O or S, then p and/or q are 0, respectively;
$Q^1$, $Q^2$, $Q^3$ and $Q^4$ are linkers, such as hydrocarbylene (including substituted hydrocarbylene, heteroatom containing hydro-carbylene, substituted heteroatom containing hydro-carbylene) or —(CO)—, and two or more substituents on adjacent atoms within $Q^1$, $Q^2$, $Q^3$ and $Q^4$ may be linked to form an additional cyclic group;
s, t, u, v are each 0 or 1; and
$R^3$, $R^4$, $R^5$ and $R^6$ are each selected independently from the group consisting of hydrogen, hydrocarbyl, substituted hydrocarbyl, heteroatom containing hydro-carbyl, substituted heteroatom containing hydro-carbyl, and functional groups.
Preferably the catalyst is of the formula:

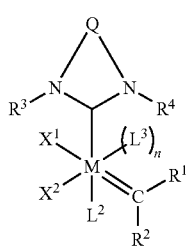

(XIII)

wherein
M, $L^2$, $L^3$, n, $X^1$, $X^2$, $R^1$, $R^2$ are as defined previously; and
Preferably at least one, and more preferably both, of the substituents $R^3$ and $R^4$ are alicyclic or aromatic and may or may not contain heteroatoms and/or substituents.

Q is a linker so that the entire ligand is an N-heterocyclic Carbene (NHC) ligand. Q is selected from the group consisting of hydrocarbylenes, substituted hydrocarbylenes, heteroatom containing hydro-carbylenes, and substituted heteroatom containing hydrocarbylenes, where two or more adjacent substituents in Q may be linked to form a polycyclic structure of two or more fused rings.

Another preferred catalytic material of step ii) comprises a catalyst of the formula:

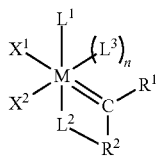

(XIV)

wherein
M, $L^2$, $L^3$, n, $X^2$, $R^1$, $R^2$ are as defined previously; and
$L^2$ and $R^2$ are linked to form a bidentate ligand.
Preferably the catalytic material of step ii) comprises a compound of the formula:

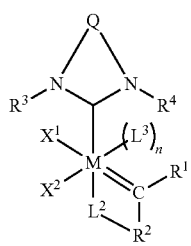

(XV)

wherein
M, $L^1$, $L^2$, $L^3$, n, $X^1$, $X^2$, $R^1$, $R^2$, $R^3$, $R^4$ and Q are as defined previously; and
$L^2$ and $R^2$ are linked to form a bidentate ligand.
In the formulas of the catalysts given in formulas (X) to (XIV), the references to $R^1$ $R^2$ and X are different from those $R^1$ $R^2$ and X mentioned in formulas (I) to (IX) mentioned in the processes and should not be used to interpret the claims.

In an aspect of the invention the process of preparing 2,5-dihydroxy-hex-3-enedioic acid or esters thereof comprises the steps of:
a) Providing a feedstock solution of a sugar composition;
b) Converting the sugar in the presence of a metallosilicate material and one or more metal ions, such as one or more of potassium ion, sodium ion, lithium ion, rubidium ion and caesium ion, to obtain a product;
c) providing a catalyst material catalyzing a metatesis reaction;
d) converting the product of b) in the presence of the catalytic material of c)
e) v recovering the reaction product comprising 2,5-dihydroxy-hex-3-enedioic acid or esters thereof.

The sugar composition preferably comprises one or more C6 and/or C5 and/or C4 and/or C3 and/or C2 saccharide units selected from the group consisting of sucrose, xylose, mannose, tagatose, galactose, glucose, fructose, sugar syrup, threose, erythrose, erythrulose, dihydroxyacetone, glyceraldehyde and glycolaldehyde.

Suitable metallo silicate materials are those capable of converting the saccharide units into compound (II). See e.g. WO 2016/083137 for details on the conversion of the saccharide units into compound (II) which also suggest suitable reaction conditions for steps a) and b) above. For steps c) to e) above, the same reaction conditions apply as stated previously.

There will be bi-products in the product obtained in step b). It will comprise e.g. methyl lactate and/or ethyl lactate in various amounts. Therefore, the product of step b) may optionally be subjected to a purification step in which the concentration of a compound corresponding to formula II is increased prior to being contacted with the material catalyzing a metathesis reaction of step c).

Specific catalysts useful in the process according to the present invention are e.g.:

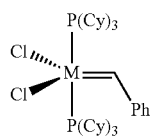

(XVI)

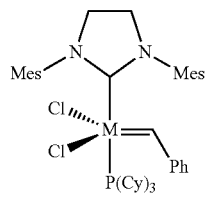

(XVII)

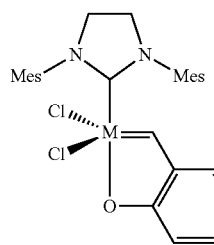

(XVIII)

As exemplified herein, catalytic homo metathesis of the compound of formula II using Grubbs-type catalysts (including Grubbs $1^{st}$, Grubbs $2^{nd}$ and Hoveyda-Grubbs catalysts) affords the compound of formula I in excellent yield and with meso stereochemical configuration.

The metathesis reaction can be carried out industrially in a stirred tank reactor. When a stirred tank reactor is used, the feed comprising the compound of formula (II) or the compound of formula (VI), such as methyl vinyl glycolate, is preferably loaded into the tank containing the metathesis catalyst material, and the temperature may be adjusted in order to optimize the reaction rate and maintain a high productivity for the catalyst present in the tank. Preferably, the reactor comprises a mechanical stirrer, which provides a thorough mixing of the entire reaction mixture in order to keep the catalyst in constant contact with the substrate and avoid heterogeneities to develop in the reaction mixture. The formed ethylene co-product is continuously leaked from the reactor to avoid ethylene poisoning of the metathesis catalyst and to avoid any pressure build-up, and the ethylene may be compressed and collected for other use if desired. The entire metathesis reaction may be performed either as a batch process or continuously. It can be performed continuously by constantly feeding the feedstock and fresh catalyst to the reactor, while collecting precipitated metathesis product, and optionally also catalyst, at a similar rate. The collected metathesis product may be drained for unconverted substrate and catalyst, which may be recycled to the reactor. The catalyst collected, may be subjected to a regeneration or reactivation process.

Alternative processes can be envisaged so long as they are industrially applicable.

Definitions

In the present context, "adipate type compounds" are meant to refer to any compound consisting of a $C_6$-chain which has either two carboxylic acid groups, one ester and one carboxylic acid group or two ester groups, placed in a 1,6-relationship to each other. The carbon chain may be saturated or unsaturated and it may contain substituents on 0, 1, 2, 3 or 4 of the four available carbon-atoms. The substituents may be selected from a group consisting of hydrocarbyl, substituted hydrocarbyl, heteroatom containing hydrocarbyl, hydroxyl, hetero atoms and functional groups.

The reference to "a compound (I)" is meant to refer to "a compound of the formula (I)". And similarly for reference to compound (II) etc.

The term "vinyl glycolate substrate" is meant to refer to vinyl glycolic acid, 2-hydroxy but-3-enoic acid, or an ester hereof. In general, the term substrate is meant to refer to the compound of formula (II) or to the compound of formula (IV).

The term "catalyst material catalyzing a metathesis reaction" is meant to refer to any compound which catalyzes a metathesis reaction such as described in US 2009/0264672. It may also be referred to as a "metathesis catalyst" or a "metathesis catalyst material".

The "percentage loading of catalyst" in the reactor may be defined as the percentage (mol/mol) of the catalyst compared to the substrate.

The "yield" is calculated as a percentage (mol/mol) of the maximum theoretical yield of the reaction ($Y_{max}$=mol compound II/2).

The term "without the addition of solvent" is meant to refer to avoiding to dilute the substrate for the process, i.e. to retain a high concentration of substrate. In practice, the substrate may be provided in a form which comprises bi-products. The bi-products may originate from the preparation of that component. I.e. the substrate may not be pure. If the substrate is produced by conversion of sugar, it may e.g. be provided in a form which comprises e.g. methyl lactate and/or ethyl lactate in various amounts. In practice the compound (II) will be present in the feed at a concentration of at least 50 wt % and the rest may be other products from the preparation of compound (II), e.g. alkyl lactates, such as methyl and/or, ethyl lactate. Preferably, the feed comprises from 50 to 100 wt % of the compound (II), such as from 70 to 100, 80 to 100 or 95 to 100 wt %. When the feed has been mixed with the catalyst material to form a reaction mixture, the concentration of substrate will be slightly lower, the lowering depending on the catalyst loading. However, high purity of substrate in the reaction mixture allows low loading of catalyst, yet retaining the high yields. When the process is carried out in a continuous manner, the concentration of compound (II) in the reaction mixture is in the same range, since the reaction product of formula (I) will precipitate from the reaction mixture and may be recovered on a continuous basis. "Without the addition of solvent" may also be referred to as "solvent-free".

The "reaction mixture" is meant to refer to the mixture wherein the conversion of compound (II) into compound (I) takes place in the presence of the catalytic material. It may include a solvent if such has been added. Preferably, the reaction mixture refers to the mixture contained in the reaction vessel in which the conversion takes place.

The term "feed" is meant to refer to the fluid added to the reaction vessel comprising the compound of formula (II) or the compound of formula (VI). The feed may also comprise a solvent.

In the present context, the terms "reacting" and "converting" is meant to refer to the same and the terms "reaction" and "conversion" is meant to refer to the same.

EXAMPLE

Example 1: Preparation of 2,5-dihydroxy-hex-3-enedioic acid dimethyl ester

In a clean dry glass flask equipped with a coldfinger condenser and a spigot suitable for connection to a vacuum outlet/gas inlet was placed a magnetic stirbar and the metathesis catalyst. The flask was evacuated and purged with dry nitrogen several times. Methyl Vinyl Glycolate (the substrate) and optionally solvent (examples 3, 4 and 5) was added to the reaction vessel by the use of a syringe to form a reaction mixture. The reaction mixture was heated in an oil bath at 80° C. for 18 hours under a nitrogen atmosphere. After cooling to room temperature the metathesis product was obtained (or recovered) as a colorless solid. The compound was purified by recrystallization from ethyl acetate. All of the Grubbs catalysts used are ruthenium based.

TABLE 1

Yield of 2,5-dihydroxy-hex-3-enedioic acid dimethyl ester from MVG.

| | Catalyst | Loading/ mol % | Amount of substrate/ mmol | Solvent/ relative volume | Yield/ mol % |
|---|---|---|---|---|---|
| 1 | Grubbs 1st gen. | 5 | 10 | — | 8% |
| 2 | Grubbs 2nd gen. | 0.3 | 5 | — | 74% |
| 3 | Grubbs 2nd gen. | 0.3 | 2.5 | Toluene 1:1 | 55% |
| 4 | Grubbs 2nd gen. | 0.3 | 5 | Toluene 2:1 | 63% |
| 5 | Grubbs 2nd gen. | 2.2 | 2.5 | EtOAc 4:1 | 46% |
| 6 | Grubbs 2nd gen. | 0.4 | 10 | — | 75% |
| 7 | Grubbs 2nd gen. | 0.4 | 19 | — | 85% |
| 8 | Grubbs 2nd gen. | 0.4 | 39 | — | 88% |
| 9 | Hoveyda-Grubbs 2nd gen. | 0.4 | 2.5 | — | 73% |
| 10 | Hoveyda-Grubbs 2nd gen. | 0.4 | 19 | — | 93% |
| 11 | Hoveyda-Grubbs 2nd gen. | 0.2 | 19 | — | 90% |
| 12 | Hoveyda-Grubbs 2nd gen. | 0.05 | 20 | — | 77% |
| 13 | Hoveyda-Grubbs 2nd gen. | 0.045 | 39 | — | 80% |

The resulting product has 2 stereocenters, corresponding to three different stereoisomers, of which one is a meso form. Taking into account the possibility of forming both the (E)- and the (Z)-isomer, the total number of different isomers amounts to six. Surprisingly, the reaction yields only one isomeric form of the product, which was determined by X-ray diffraction to be the meso form of the (E)-isomer. NMR spectra of the crude reaction mixture show no signals from a (Z)-double bond, and a GC of the crude reaction mixture show no presence of other diastereomeric forms.

It appears from rows 3, 4 and 5 that the yields are lower, when a solvent is addet to the reaction mixture.

Example 2: Preparation of a Compound of Formula (VII) from MVG

In a 50 ml round bottomed flask is put 5.0 g of MVG (43.1 mmol), 1.3 g of ethylene glycol (21.0 mmol) and 25 ml of anhydrous toluene. Finally, 500 mg of strongly acidic resin is added (Amberlyst 15) and the product mixture is refluxed gently for one hour. The flask is fitted with a distillation head and over the course of two hours, 15 ml of liquid is distilled from the flask. The residue is cooled to room temperature and filtered and then concentrated to obtain around 5 ml of liquid product which is purified by column chromatography to obtain the diester of ethylene glycol and vinyl glycolic acid (compound (VII).

Example 3: Preparation of 6,9-dihydroxy-2,3,6,9-tetrahydro-[1,4]dioxecine-5,10-dione (Compound (VIII))

compound (VIII) is made according to this method:
In a 25 ml round bottomed flask containing 10 ml toluene is added 2.26 g of 2-hydroxybut-3-enoic acid 2-(2-hydroxy-but-3-enoyloxy)-ethyl ester (compound VII) and 31.0 mg of Hoveyda Grubbs $2^{nd}$ generation catalyst under argon atmosphere (0.5% loading). The flask is heated on an oil bath at 80° C. for 18 hours. Analysis of the reaction mixture by GCMS shows that the starting material is almost completely converted and a new peak with M/Z 198, corresponding to compound (VIII) appears.

Example 4: Preparation of 7,10-dihydroxy-1,5-di-oxa-cycloundec-8-ene-6,11-dione (Compound (X))

compound (X) is made according to this method:
In a 25 ml round bottomed flask containing 10 ml toluene is added 2.40 g of 2-hydroxybut-3-enoic acid 3-(2-hydroxy-but-3-enoyloxy)-propyl ester (compound IX) and 31.0 mg of Hoveyda Grubbs $2^{nd}$ generation catalyst under argon atmosphere (0.5% loading). The flask is heated on an oil bath at 80° C. for 18 hours. Analysis of the reaction mixture by GCMS shows that the starting material is almost completely converted and a new peak with M/Z 212, corresponding to compound (X) appears.

EMBODIMENTS

Embodiment 1

A compound of the formula I:

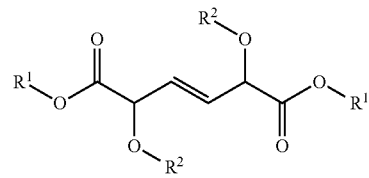

wherein

R¹ is selected from the group consisting of H—; and C₁-C₁₂ alkyl; optionally substituted with a heteroatom selected from N, O, F, P, S, Cl, Br, and I;

R² is selected from the group consisting of —H; and —CH₃.

Embodiment 2

The compound according to embodiment 1, wherein R² is —H.

Embodiment 3

The compound according to any one of embodiments 1 or 2, wherein R¹ is selected from the group consisting of —H, —CH₃ or —CH₂CH₃, —C₃H₇ and —C₄H₉.

Embodiment 4

The compound according to embodiment 1, wherein R¹ and R² each are —CH₃.

Embodiment 5

The compound according to any one of embodiments 1 to 4, wherein the double bond is (E) configuration.

Embodiment 6

A process for preparing the compound according to any one of embodiments 1 to 5 comprising the steps of:
a. providing a compound of the formula:

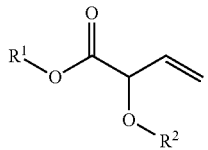

wherein

R¹ is selected from the group consisting of H—; and C₁-C₁₂ alkyl; optionally substituted with a heteroatom selected from O, N, S, F, Cl, Br, and I;

R² is selected from the group consisting of —H; and —CH₃;

b. providing a catalyst material catalysing a metathesis reaction;
c. converting the compound of i) in the presence of the catalytic material of ii); and
d. recovering the reaction product.

Embodiment 7

The process according to embodiment 6, wherein the conversion temperature of iii) is in the range of from 20 to 120° C.

Embodiment 8

The process according to any one of embodiments 6 or 7, wherein step iii) is continued for a period of time in the range of from 5 minutes to 24 hours.

Embodiment 9

The process according to any one of embodiments 6 to 8, wherein the conversion step of iii) is conducted without the addition of solvent.

Embodiment 10

The process according to any one of embodiments 6 to 8, wherein the conversion step of iii) is conducted in the presence of an alkyl lactate, such as methyl, ethyl lactate or a mixture thereof.

Embodiment 11

The process according to any one of embodiments 6 to 10, wherein the catalytic material of step ii) comprises a compound of the formula:

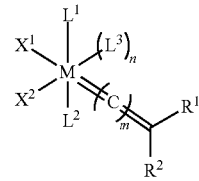

wherein

M is a transition metal, for example ruthenium, molybdenum, osmium, chromium, rhenium and tungsten, preferably a group 8 transition metal;

L² and L³ are neutral electron donor ligands;

n is 0 or 1;

m is 0, 1 or 2;

X¹ and X² are anionic ligands;

R¹ and R² are each selected independently from the group consisting of hydrogen, hydrocarbyl, substituted hydrocarbyl, heteroatom containing hydro-carbyl, substituted heteroatom containing hydro-carbyl, and functional groups; and L¹ is a carbene of the formula:

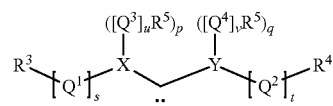

Wherein

Y and Z are heteroatoms, such as N, O, S or P, and if X and/or Y are O or S, then p and/or q are 0, respectively, Q1, Q2, Q3 and Q4 are linkers, such as hydrocarbylene (including substituted hydrocarbylene, heteroatom containing hydro-carbylene, substituted heteroatom containing hydro-carbylene) or —(CO)—, and two or more substituents on adjacent atoms within Q1, Q2, Q3 and Q4 may be linked to form an additional cyclic group;

s, t, u, v are each 0 or 1

R3, R4, R5 and R6 are each selected independently from the group consisting of hydrogen, hydrocarbyl, substituted hydrocarbyl, heteroatom containing hydrocarbyl, substituted heteroatom containing hydro-carbyl, and functional groups.

Embodiment 12

The process according to embodiment 11, wherein the catalytic material of step ii) comprises a compound of the formula:

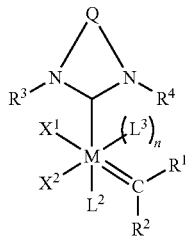

wherein
M, L2, L3, n, X1, X2, R1, R2 are as defined previously, and
Preferably at least one, and more preferably both, of the substituents R3 and R4 are alicyclic or aromatic and may or may not contain heteroatoms and/or substituents.
Q is a linker selected from the group consisting of hydrocarbylenes, substituted hydrocarbylenes, heteroatom containing hydro-carbylenes, and substituted heteroatom containing hydrocarbylenes, where two or more adjacent substituents in Q may be linked to form a polycyclic structure of two or more fused rings, so that the entire ligand is an N-heterocyclic Carbene (NHC) ligand.

Embodiment 13

The process according to any one of embodiments 6 to 10, wherein the catalytic material of step ii) comprises a compound of the formula:

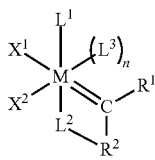

Wherein
M, L1, L2, L3, n, X1, X2, R1, R2 are as defined previously, and L2 and R2 are linked to form a bidentate ligand.

Embodiment 14

The process according to embodiment 13, wherein the catalytic material of step ii) comprises a compound of the formula:

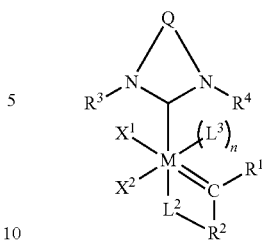

Wherein
M, L1, L2, L3, n, X1, X2, R1, R2, R3, R4 and Q are as defined previously, and L2 and R2 are linked to form a bidentate ligand.

Embodiment 15

The process according to any one of embodiments 6 to 14 conducted under continuous conditions.

Embodiment 16

A process of preparing 2,5-dihydroxy-hex-3-enedioic acid or esters thereof comprising the steps of:
i. Providing a feedstock solution of a sugar composition;
ii. Converting the sugar in the presence of a metallo-silicate material and one or more metal ions, such as one or more of potassium ion, sodium ion, lithium ion, rubidium ion and caesium ion;
iii. providing a catalyst material catalysing a metatesis reaction;
iv. converting the compound of i) in the presence of the catalytic material of ii)
iv) recovering the reaction product.

The invention claimed is:

1. A compound of the formula I:

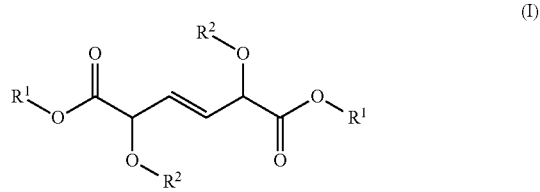

(I)

wherein either:
R$^1$ is selected from the group consisting of —H and C$_1$-C$_2$ alkyl; and
R$^2$ is —CH$_3$,
or
R$^1$ is CH$_3$; and
R$^2$ is selected from the group consisting of —H and —CH$_3$.

2. The compound according to claim 1, wherein R$^1$ is —CH$_3$ and R$^2$ is —H.

3. The compound according to claim 1, wherein R$^1$ is selected from the group consisting of —H, —CH$_3$, and —CH$_2$CH$_3$ and R$^2$ is —CH$_3$.

4. The compound according to claim 1, wherein R$^1$ and R$^2$ each are —CH$_3$.

5. The compound according to claim 1, wherein the C—C double bond of Compound (I) is in (E) configuration.

6. A composition comprising a compound of formula (I) according to claim 1.

7. The composition according to claim 6, further comprising a solvent.

8. The composition according to claim 6, wherein at least 80 wt % of the compound of formula (I) is in (E)-configuration.

9. A process comprising the steps of:
i) providing a compound of the formula:

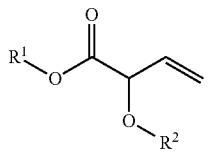
(II)

wherein
$R^1$ is selected from the group consisting of —H and $C_1$-$C_2$ alkyl; and
$R^2$ is selected from the group consisting of —H and —$CH_3$;
ii) providing a catalyst material catalyzing a metathesis reaction;
iii) converting the compound of i) in the presence of the catalytic material of ii); and
iv) recovering a reaction product comprising a compound of formula (I):

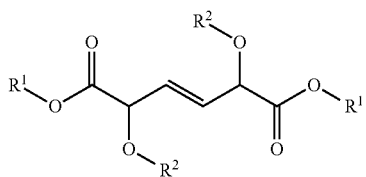
(I)

wherein $R^1$ and $R^2$ are as defined in formula (II).

10. The process according to claim 9, wherein the conversion temperature of iii) is in the range of from 20 to 120° C.

11. The process according to claim 9, wherein step iii) is continued for a period of time in the range of from 5 minutes to 24 hours.

12. The process according to claim 9, wherein the conversion step of iii) is conducted at a pressure in the range of from 1 to 1000 kPa.

13. The process according to claim 9, wherein the conversion step of iii) is conducted without the addition of solvent.

14. The process according to claim 13, wherein the compound of the formula (II) is provided in a feed comprising at least 50 wt % of the compound (II).

15. The process according to claim 9, wherein the conversion step of iii) is conducted in the presence of an alkyl lactate.

16. The process according to claim 9 conducted under continuous conditions.

17. The process according to claim 9, wherein:
$R^1$ is —H; and
$R^2$ is —H.

18. The process according to claim 9, wherein:
$R^1$ is —H; and
$R^2$ is —$CH_3$.

19. The process according to claim 9, wherein:
$R^1$ is —$CH_3$; and
$R^2$ is —H.

20. The process according to claim 9, wherein:
$R^1$ is —$CH_3$; and
$R^2$ is —$CH_3$.

21. The process according to claim 9, wherein:
$R^1$ is —$CH_2CH_3$; and
$R^2$ is —H.

22. The process according to claim 9, wherein:
$R^1$ is —$CH_2CH_3$; and
$R^2$ is —$CH_3$.

23. The compound according to claim 1, wherein $R^1$ is —H and $R^2$ is —$CH_3$.

24. The compound according to claim 1, wherein $R^1$ is —$CH_2CH_3$ and $R^2$ is —$CH_3$.

* * * * *